US007384981B2

(12) United States Patent
Kiliaan et al.

(10) Patent No.: US 7,384,981 B2
(45) Date of Patent: Jun. 10, 2008

(54) PREPARATION FOR IMPROVING THE ACTION OF RECEPTORS

(75) Inventors: Amanda Johanne Kiliaan, Nijmegen (NL); Robert Johan Joseph Hageman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 10/495,341

(22) PCT Filed: Nov. 14, 2002

(86) PCT No.: PCT/NL02/00731

§ 371 (c)(1),
(2), (4) Date: May 13, 2004

(87) PCT Pub. No.: WO03/041701

PCT Pub. Date: May 22, 2003

(65) Prior Publication Data

US 2005/0009779 A1   Jan. 13, 2005

(30) Foreign Application Priority Data

Nov. 14, 2001   (NL) .................................. 1019368

(51) Int. Cl.
| | |
|---|---|
| A61K 31/70 | (2006.01) |
| A61K 31/28 | (2006.01) |
| A61K 31/20 | (2006.01) |
| A61K 33/24 | (2006.01) |
| A61K 33/32 | (2006.01) |
| A61K 33/06 | (2006.01) |
| A01N 43/04 | (2006.01) |
| A01N 55/02 | (2006.01) |
| A01N 37/00 | (2006.01) |
| A01N 59/16 | (2006.01) |
| A01N 59/06 | (2006.01) |

(52) U.S. Cl. .................. 514/558; 514/52; 514/494; 514/904; 424/617; 424/641; 424/682

(58) Field of Classification Search .................. 514/52, 514/494, 558, 904, 78, 943, 924; 424/617, 424/641, 682, 439, 450
See application file for complete search history.

(56) References Cited

U.S. PATENT DOCUMENTS

| | | | | |
|---|---|---|---|---|
| 4,465,669 | A | * | 8/1984 | Wissler et al. ................. 514/21 |
| 4,544,559 | A | * | 10/1985 | Gil et al. ....................... 426/72 |
| 4,921,877 | A | * | 5/1990 | Cashmere et al. ........... 424/439 |
| 5,200,218 | A | * | 4/1993 | Lasater et al. ................. 426/72 |
| 5,612,074 | A | * | 3/1997 | Leach ............................ 426/74 |
| 5,891,465 | A | * | 4/1999 | Keller et al. ................. 424/450 |
| 6,620,850 | B2 | * | 9/2003 | Martynyuk et al. ......... 514/567 |
| 6,989,376 | B2 | * | 1/2006 | Watkins et al. ................ 514/50 |
| 2002/0182196 | A1 | * | 12/2002 | McCleary ..................... 424/94.1 |

FOREIGN PATENT DOCUMENTS

| | | |
|---|---|---|
| AU | 767364 | 2/2004 |
| AU | 770008 | 7/2004 |
| AU | 770359 | 7/2004 |
| AU | 771884 | 8/2004 |
| EP | 1 155 620 | 11/2001 |
| FR | 1325596 | 6/1962 |
| FR | 2 773 484 | 7/1999 |
| GB | 2398321 A | 8/2004 |
| GB | 2398322 A | 8/2004 |
| GB | 2398323 A | 8/2004 |
| GB | 2399120 A | 9/2004 |
| GB | 2399579 A | 9/2004 |
| GB | 2399580 A | 9/2004 |
| GB | 2399848 A | 9/2004 |
| GB | 2399849 A | 9/2004 |
| GB | 2399850 A | 9/2004 |
| GB | 2403971 A | 1/2005 |
| GB | 2403972 A | 1/2005 |
| GB | 2404676 A | 2/2005 |
| JP | 3-94655 | 4/1991 |
| JP | 5-252899 | 10/1993 |
| JP | 10-4918 | 1/1998 |
| WO | WO 98/48788 | 11/1998 |
| WO | WO 99/04782 | 2/1999 |
| WO | WO 99/37155 | 7/1999 |
| WO | WO 00/66133 | 11/2000 |
| WO | WO 01/03696 | 1/2001 |

(Continued)

OTHER PUBLICATIONS

Rathbone et al. Trophic effects of purines in neurons and glial cells. Progress in Neurobiology 1999, 59, 663-690.*

(Continued)

*Primary Examiner*—Johann Richter
*Assistant Examiner*—Ernst V Arnold
(74) *Attorney, Agent, or Firm*—Young & Thompson

(57) ABSTRACT

The present invention relates to the use of polyunsaturated fatty acids and one or more components which have a beneficial effect on total methionine metabolism selected from the group consisting of vitamin B12 and precursors thereof, vitamin B6 and derivatives thereof, folic acid, zinc and magnesium, in the manufacture of a preparation for improving the action of receptors. This preparation is advantageously applied in patients suffering from Parkinson's disease, Huntington's chorea, epilepsy, schizophrenia, paranoia, depression, sleep disorders, impaired memory function, psychoses, dementia and ADHD.

10 Claims, No Drawings

FOREIGN PATENT DOCUMENTS

| | | |
|---|---|---|
| WO | WO01/04520 A1 | 1/2001 |
| WO | WO01/21929 A1 | 3/2001 |
| WO | WO 01/24772 | 4/2001 |
| WO | WO01/33037 A1 | 5/2001 |
| WO | WO01/60545 A1 | 8/2001 |
| WO | WO 01/84961 | 11/2001 |
| WO | WO01/98623 A1 | 12/2001 |
| WO | WO02/01102 A1 | 1/2002 |
| WO | WO02/10550 A1 | 2/2002 |
| WO | WO02/10551 A1 | 2/2002 |
| WO | WO02/29199 A1 | 4/2002 |
| WO | WO02/059456 A1 | 8/2002 |
| WO | WO02/066783 A1 | 8/2002 |
| WO | WO02/068792 A1 | 9/2002 |
| WO | WO03/016669 A2 | 2/2003 |
| WO | WO03/016669 A3 | 2/2003 |
| WO | WO03/023178 A3 | 3/2003 |
| WO | WO03/042487 A3 | 5/2003 |
| WO | WO03/058022 A3 | 7/2003 |
| WO | WO03/071086 A3 | 8/2003 |
| WO | WO03/078785 A3 | 9/2003 |
| WO | WO03/086675 A3 | 10/2003 |
| WO | WO03/093623 A2 | 11/2003 |
| WO | WO03/093623 A3 | 11/2003 |
| WO | WO03/104601 A3 | 12/2003 |
| WO | WO03/106130 A3 | 12/2003 |
| WO | WO2004/010039 A3 | 1/2004 |
| WO | WO2004/011776 A3 | 2/2004 |
| WO | WO2004/018823 A3 | 3/2004 |
| WO | WO2004/018824 A3 | 3/2004 |
| WO | WO2004/023014 A3 | 3/2004 |
| WO | WO2004/026017 A3 | 4/2004 |
| WO | WO2004/026073 A3 | 4/2004 |
| WO | WO2004/026500 A3 | 4/2004 |
| WO | WO2004/027200 A2 | 4/2004 |
| WO | WO2004/027200 A3 | 4/2004 |
| WO | WO2004/027204 A3 | 4/2004 |
| WO | WO2004/027205 A3 | 4/2004 |
| WO | WO2004/027786 A2 | 4/2004 |
| WO | WO2004/027786 A3 | 4/2004 |
| WO | WO2004/053434 A2 | 6/2004 |
| WO | WO2004/053434 A3 | 6/2004 |
| WO | WO2004/067961 A2 | 8/2004 |
| WO | WO2004/074622 A2 | 9/2004 |
| WO | WO2004/076798 A2 | 9/2004 |
| WO | WO2004/081346 A2 | 9/2004 |
| WO | WO2004/083591 A2 | 9/2004 |
| WO | WO2004/083592 A2 | 9/2004 |
| WO | WO2004/083593 A2 | 9/2004 |
| WO | WO2004/083594 A2 | 9/2004 |
| WO | WO2004/085790 A2 | 10/2004 |
| WO | WO2004/089608 A2 | 10/2004 |
| WO | WO2004/092527 A2 | 10/2004 |
| WO | WO2004/092528 A2 | 10/2004 |
| WO | WO2004/092530 A2 | 10/2004 |
| WO | WO2004/094766 A2 | 11/2004 |
| WO | WO2005/017303 A2 | 2/2005 |
| WO | WO2005/021921 A2 | 3/2005 |
| WO | WO2005/021922 A2 | 3/2005 |

OTHER PUBLICATIONS

Pettegrew et al. Clinical and Neurochemical effects of acetyl-l-carnitine in Alzheimer's disease Neurobiology of Aging 1995, 16(1), 1-4.*
Answers.com Huperzine A [online] [retrieved on Oct. 4, 2005] retrieved from the internet: http://www.answers.com/topic/huperzine-a.*
International Examination Report, Application PCT/US03/04837, Dec. 9, 2004.
International Examination Report, Application PCT/US03/11765; Dec. 10, 2004.
International Examination Report, Application PCT/US03/11765;; Jan. 25, 2005.
International Examination Report, Application PCT/US03/13787; Mar. 2, 2005.
International Search Report, Application PCT/US03/25716; Jan. 13, 2005.
International Search Report, Application PCT/US03/25742; Dec. 20, 2004.
International Examination Report, Application PCT/US03/29460; Dec. 8, 2004.
Search Report to Application No. EP 02806451.7; Feb. 9, 2005.
Examination Report to Application GB 0220872.6, Oct. 29, 2004.
Examination Report to Application No. GB 0225505.7, Oct. 27, 2004.
Examination Report to Application No. GB 0225505.7 Feb. 15, 2005.
Examination Report to Application No. GB 0306046.4, Sep. 10, 2004.
Examination Report to Application No. GB 0400018.8; Oct. 29, 2004.
Examination Report to Application No. GB 0400019.6; Oct. 29, 2004.
Examination Report to Application No. GB 0403891.5, Feb. 14, 2005.
Examination Report to Application No. GB 0403894.9, Feb. 15, 2005.
Examination Report to Application No. GB 0403921.0, Feb. 15, 2005.
Examination Report to Application No. GB 0406257.6, Jan. 25, 2005.
Examination Report to Application No. GB 0406258.4; Jan. 12, 2005.
Examination Report to Application No. GB 0411698.4, Jan. 24, 2005.
Search Report to Application No. GB 0415835.8, Dec. 2, 2004.
Examination Report to Application No. 0416625.2 Jan. 20, 2005.
Search and Examination Report to Application No. GB 0416834.0, Nov. 16, 2004.
Examination Report to Application No. GB 0422419.2 Dec. 8, 2004.
Search and Examination Report to Application No. GB 0422893.8 Nov. 24, 2004.
Search and Examination Report to Application No. GB 0423416.7 Nov. 12, 2004.
Search and Examination Report to Application No. GB 0423417.5 Nov. 12, 2004.
Search and Examination Report to Application No. GB 0423418.3 Nov. 12, 2004.
Search and Examination Report to Application No. GB 0426155.8 Jan. 12, 2005.
Search and Examination Report to Application No. GB 0426156.6 Jan. 12, 2005.
Search and Examination Report to Application No. GB 0426157.4 Jan. 12, 2005.
Examination Report to Application No. GB 0428141.6 Feb. 9, 2005.
Examination Report to Application No. GB 0500184.7 Feb. 9, 2005.
Search and Examination Report to Application No. GB 0500600.2 Feb. 15, 2005.
Written Opinion to Application No. PCT/US02/25608 Feb. 2, 2005.
Written Opinion to Application No. PCT/US02/25675 Nov. 24, 2004.
Written Opinion to Application No. PCT/US02/39425; Nov. 22, 2004.
Written Opinion to Application No. PCT/US03/06544; Feb. 18, 2005.
Written Opinion to Application No. PCT/US03/13787 Nov. 9, 2004.
Written Opinion to Application No. PCT/US03/14153 Nov. 9, 2004.
Written Opinion to Application No. PCT/US03/18530 Sep. 13, 2004.
Written Opinion to Application No. PCT/US03/19993 Oct. 15, 2004.

Written Opinion to Application No. PCT/US03/38550 Dec. 10, 2004.
Combined Search Report and Written Opinion to Application No. PCT/US04/02122 Feb. 24, 2005.
Combined Search Report and Written Opinion to Application No. PCT/US04/04740 Jan. 19, 2005.
Combined Search Report and Written Opinion to Application No. PCT/US04/06246 Jan. 26, 2005.
Combined Search Report and Written Opinion to Application No. PCT/US04/08030 Jan. 6, 2005.
Combined Search Report and Written Opinion to Application No. PCT/US04/08073 Mar. 4, 2005.
Combined Search Report and Written Opinion to Application No. PCT/US04/08170 Jan. 13, 2005.
Combined Search Report and Written Opinion to Application No. PCT/US04/08171 Feb. 16, 2005.
Combined Search Report and Written Opinion to Application No. PCT/US04/11172 Feb. 14, 2005.
Combined Search Report and Written Opinion to Application No. PCT/US04/28438 Mar. 14, 2005.
International Examination Report, Application PCT/US02/24399, Aug. 6, 2004.
Examination Report, Application PCT/US02/25727; Jul. 7, 2004.
Examination Report, Application PCT/US03/10144; Jul. 7, 2004.
International Search Report, Application PCT/US03/18530; Jun. 24, 2004.
International Search Report, Application PCT/US03/20870; Sep. 30, 2004.
International Examination Report, Application PCT/US03/25676, Aug. 17, 2004.
International Examination Report, Application PCT/US03/25677, Aug. 17, 2004.
International Search Report, Application PCT/US03/25707; Jun. 23, 2004.
International Search Report, Application PCT/US03/25715; Apr. 9, 2004.
International Search Report, Application PCT/US03/25742; May 27, 2004.
International Search Report, Application PCT/US03/29460; May 25, 2004.
International Search Report, Application PCT/US03/25667; Feb. 26, 2004.
International Search Report, Application PCT/US03/29858; Jun. 30, 2003.
International Search Report, Application PCT/US03/29859; May 21, 2004.
International Examination Report, Application PCT/US03/29859, Aug. 16, 2004.
International Search Report, Application PCT/US03/38550; Jun. 15, 2004.
Examination Report to Application No. GB 0208367.3, Jan. 30, 2004.
Examination Report to Application No. GB 0219757.2, May 10, 2004.
Examination Report to Application No. GB 0314846.7, Jul. 15, 2004.
Examination Report to Application No. GB 0320747.9, May 25, 2004.
Search and Examination Report to Application No. GB 0403891.5, Jun. 9, 2004.
Search and Examination Report to Application No. GB 0403893.1, Jun. 9, 2004.
Search and Examination Report to Application No. GB 0403894.9, Jun. 9, 2004.
Search and Examination Report to Application No. GB 0403897.2, Jun. 9, 2004.
Search and Examination Report to Application No. GB 0403920.2, Jun. 10, 2004.
Search and Examination Report to Application No. GB 0403921.0, Jun. 10, 2004.
Search and Examination Report to Application No. GB 0403926.9, Jun. 10, 2004.
Examination Report to Application No. GB 0404796.5; May 20, 2004.
Search and Examination Report to Application No. GB 0404833.6, Aug. 19, 2004.
Search and Examination Report to Application No. GB 0404837.7, May 17, 2004.
Examination Report to Application No. GB 0404837.7, Jul. 12, 2004.
Search and Examination Report to Application No. GB 0404839.3, May 14, 2004.
Search and Examination Report to Application No. GB 0404842.7, May 14, 2004.
Search and Examination Report to Application No. GB 0404845.0, May 14, 2004.
Search and Examination Report to Application No. GB 0404849.2, May 17, 2004.
Examination Report to Application No. GB 0406257.6, Jun. 28, 2004.
Examination Report to Application No. GB 0406258.4, May 20, 2004.
Examination Report to Application No. GB 0408672.4, Jul. 12, 2004.
Examination Report to Application No. GB 0404830.2, Aug. 17, 2004.
Search and Examination Report to Application No. GB 0411698.4, Jun. 30, 2004.
Search and Examination Report to Application No. GB 0411892.3, Jul. 14, 2004.
Search and Examination Report to Application No. GB 0411893.3, Jul. 14, 2004.
Search and Examination Report to Application No. GB 0411894.9, Jun. 30, 2004.
Search and Examination Report to Application No. GB 0412190.1, Jul. 22, 2004.
Search and Examination Report to Application No. GB 0412191.9, Jul. 22, 2004.
Search and Examination Report to Application No. GB 0412192.7, Jul. 22, 2004.
Search and Examination Report to Application No. GB 0416834.0, Aug. 11, 2004.
Search and Examination Report to Application No. GB 0417810.9, Aug. 25, 2004.
Search and Examination Report to Application No. GB 0417811.7, Aug. 25, 2004.
Search and Examination Report to Application No. GB 0418005.5, Aug. 25, 2004.
Search and Examination Report to Application No. GB 0418425.5, Sep. 10, 2004.
Search and Examination Report to Application No. GB 0418426.3 Sep. 10, 2004.
Search and Examination Report to Application No. GB 0418427.1 Sep. 10, 2004.
Search and Examination Report to Application No. GB 0418429.7 Sep. 10, 2004.
Search and Examination Report to Application No. GB 0418430.5 Sep. 10, 2004.
Search and Examination Report to Application No. GB 0418431.3 Sep. 10, 2004.
Search and Examination Report to Application No. GB 0418432.1 Sep. 10, 2004.
Search and Examination Report to Application No. GB 0418433.9 Sep. 10, 2004.
Search and Examination Report to Application No. GB 0418439.6 Sep. 10, 2004.
Search and Examination Report to Application No. GB 0418442.0 Sep. 10, 2004.
Written Opinion to Application No. PCT/US02/24399; Apr. 28, 2004.
Written Opinion to Application No. PCT/US02/25608 Sep. 13, 2004.
Written Opinion to Application No. PCT/US02/25727; May 17, 2004.
Written Opinion to Application No. PCT/US03/14153 Sep. 9, 2004.

Adriane Fugh-Berman, MD et al., "Dietery Supplements and Natural Products as Psychotherapeutic Agents", Psychosomatic Medicine, Elsevier, New York, US, vol. 61, No. 5, Sep. 1999, pp. 712-728, XP000890189.

Bo-Sen Feng et al., "Effect of Supplementing Four Kinds of Nutrients on Brain Development in the Embryo Rats", Journal of Liaoning Normal University (Natural Science Edition), vol. 23, No. 4, Dec. 2000, pp. 391-394, XP008003331.

Peter J. Rogers, "A Healthy Body, A Healthy Mind: Long-Term Impact of Diet on Mood and Cognitive Function", Procedings of the Nutrition Society London, GB, (Feb. 2001), vol. 1, No. 60, pp. 135-143, XP008003310.

C.B. Lombard, "What is the Role of Food in Preventing Depression and Improving Mood, Performance and Cognitive Function?", Medical Journal of Australia, XX, XX, vol. Suppl, No. 173, Nov. 6, 2000, pp. S104-S105, XP008003311.

* cited by examiner

PREPARATION FOR IMPROVING THE ACTION OF RECEPTORS

The present invention relates to a preparation for improving the action of receptors, in particular for improving the sensitivity of receptors to neurotransmitters.

Receptors can be present in the membranes of cells. The receptor is activated under the influence of components present outside the cell (for example, neurotransmitters, neuromodulators or hormones) which bind to the receptor. The receptor is then capable of transmitting signals, which can start a cascade of events. Receptors can be present, inter alia, in or on nerve cells, muscle cells, endocrine cells, epithelial cells or other types of cells. Examples of substances which have an effect on receptors are neurotransmitters (see below), neuromodulators, neuropeptides and hormones such as insulin and steroids.

A specific class of receptors is, for example, constituted by receptors in nerve cells (neurones) which are controlled by neurotransmitters. These neurones consist of a cell body (soma) with several, frequently short fimbriae (dendrites) and one long fimbria, termed an axon. An electrical signal is transmitted from the soma via the axon. The axon branches into axon ends which can terminate next to the dendrites of adjacent nerve cells, onto another axon, next to the soma of nerve cells or in tissues or parts thereof. The so-called synaptic cleft is located between the axon of the one nerve cell and the dendrite (or also soma) of the other nerve cell.

If a nerve cell is stimulated, substances can be released which are termed neurotransmitters or neuromodulators and which are able to activate another nerve cell. The neurotransmitters/neuromodulators are recognised by receptors in the postsynaptic membrane of the "receiving" nerve cell.

Examples of classic endogenous neurotransmitters are biogenic amines such as serotonin, dopamine, histamine, noradrenaline and adrenaline; amino acids such as GABA (gamma-aminobutyric acid), glutamate, aspartate and glycine; cholinergic agents, such as acetylcholine; peptides, such as endorphins and other types of neurotransmitters such as nitrogen oxide and adenosine. In addition, many substances have been found which are recognised by the neurotransmitter receptors, such as certain drugs (for example clenbuterol), which usually are prepared synthetically, but also substances from natural preparations (such as muscarine antagonists or ephedrine-rich plant extracts).

Receptors can be classified on the basis of their action. Ionotropic receptors act rapidly and determine ion transport through the membrane. They consist of a large complex of multiple sub-units made up of five individual proteins which combine to establish an ion channel through the membrane. The sub-units have four transmembrane domains which form the pore. These ion channels are impermeable to ions in the absence of a neurotransmitter.

Metabotropic receptors constitute another class. These act relatively slowly and have a wide range of effects on the metabolism of the cell. Many comprise the seven transmembrane domain receptors, which usually function via G proteins. These types of receptors play a role, inter alia, in the case of neurotransmitters which belong to the adrenergic agents (for example noradrenaline and adrenaline), in the case of dopamine, serotonin and in the case of neurotransmitters which belong to the cholinergic agents (such as acetylcholine or muscarine). Other examples of seven trans-membrane domain receptors are receptors which are activated by neuropeptides, such as by Substance P, Neuropeptide Y, Bombesine, Neurotensine, CCK and galanine.

Others include single transmembrane domain receptors such as the tyrosine kinase receptor family (growth factors, insulin), the cytokine receptor family (growth hormone, erythropoietin, leptin, prolactin), the serine-threonine kinase receptor family (TGF-beta), the guanylyl cyclase receptor family (atrial natriuretic peptides) and the phosphotyrosine phosphatase family.

Many medical disorders are associated with disturbed signal transmission. This can be due to a reduced concentration of hormones and/or neurotransmitters and/or neuromodulators, but also to a reduced sensitivity of the receptor towards the specific substance.

A neurotransmitter functioning that is disturbed to a more or less severe extent can play a role in neurological disorders such as dementia, depression, Parkinson's disease, Huntington's chorea, epilepsy, schizophrenia, paranoia and ADHD, but also in other emotional disorders.

Various ways for improving the functioning of the nerve processes have been conceived in the past. For example, neurotransmitters such as dopamine or derivatives thereof have been administered to people suffering from Parkinson's disease in order to increase the amount of dopamine in the synapse. Substances have also been administered in order to reduce the reuptake of the neurotransmitter serotonin from the synaptic cleft into the dendrite. Agents which inhibit a specific metabolic conversion of the neurotransmitter acetylcholine (acetylcholinesterase inhibitors), as a result of which the concentrations of acetylcholine in the synaptic cleft (i.e. extracellular) remain high for a prolonged period, have also been described. Monoamine oxidase inhibitors partially prevent the conversion of monoamines such as dopamine.

In contrast with the aforementioned approaches, the aim of the invention is to improve the action, and especially the sensitivity of receptors, in particular in nerve processes, but also in other physiological processes in which, for example, hormones play a role. What is meant by an improved action of receptors is that less agonist, in particular less neurotransmitter, is needed to achieve the same effect. The present invention may advantageously be applied in patients who suffer from an imbalanced neurotransmitter functioning and/or neurodegenerative disorder. In addition, the invention may be applied in healthy individuals to improve the concentration and/or learning ability of these individuals.

The invention relates to the use of polyunsaturated fatty acids and components which have a beneficial effect on methionine metabolism for improving the action of receptors.

The inventors have unexpectedly found that the combined application of polyunsaturated fatty acids and methionine metabolism stimulating compounds improves the action of receptors, but not as a result of the increased production of neurotransmitter or a reduced reuptake of neurotransmitter from the synaptic cleft. According to the inventors, the surprising effect of the active principles according to the invention may be explained from the improved arrangement and more fluid nature of the cell membranes, especially of the membranes of neurons, that results from the combined administration. Because of the improved arrangement and fluidity, in vivo membrane processes can proceed more effectively after receptor activation. This improvement is not only advantageous in individuals in whom these membrane processes are adversely affected by, for instance, a neurodegenerative disorder. The improvement is also beneficial to individuals who wish to improve their ability to learn and/or concentrate, e.g. for study or work.

The treatment of a variety of disorders, including neurodegenerative disorders such as Alzheimer disease and Parkinson's disease with polyunsaturated fatty acids and vitamin B6, B12 and/or folic acid is described in WO 01/03696. In this PCT-application a link is made between an elevated serum homocysteine concentration and the undesired oxidation of essential fatty acids, in particular of eicosapentenoic acid and arachidonic acid. The administration of vitamin B6, folic acid and vitamin B12 is said to decrease the serum homocysteine concentration and consequently to diminish the oxidation of the aforementioned essential fatty acids, as a result of which, in combination with the administration of these same essential fatty acids, an increase in the serum concentration of these essential fatty acids is achieved. According to the PCT-application an increase of the concentration of essential fatty acids can be advantageous in the treatment of (a) illnesses, (b) cardiovascular or cerebrovascular disorders, (c) diabetes, syndrome X and macro or microvascular complications of diabetes, (d) psychiatric disorders, (e) neurological or neurodegenerative disorders, (f) kidney disorders, (g) inflammatory or immunological disorders of the gastrointestinal tract, (h) eye or hearing disorders, (i) forms of obesity and (j) any form of cancer. Nowhere in the PCT-application reference is made to an effect of the preparations described therein on receptor action.

Suppletion with the preparation according to the invention is beneficial in those situations where the endogenous production of neurotransmitters is marginal but the receptor is still functional, as is the case for minor manifestations of neurological disorders.

In persons suffering from serious forms of neurological disorders it is advantageous that, in addition to the aforementioned components, at least one substance is administered that increases the concentration of the neurotransmitters, neuromodulators or hormone in the synapse or at the receptor.

Polyunsaturated fatty acids are fatty acids containing at least two unsaturated bonds and having a chain length of at least 18. The unsaturated bond is located in the 3, 6 or 9 position relative to the terminal methyl group.

The preparation of the invention preferably contains $\Omega$-3 polyunsaturated fatty acids. The $\Omega$-3 polyunsaturated fatty acids include $\alpha$-linolenic acid, stearidonic acid, eicosapentaenoic acid and docosahexaenoic acid and arachidonic acid. The preparation preferably contains at least docosahexaenoic acid. For cardiovascular-associated neurological disorders such as dementia eicosapentaenoic acid is also suitably present. The daily dose of $\Omega$-3 polyunsaturated fatty acids is preferably at least 120 mg, more preferentially at least 350 mg.

The total fat composition in the preparation must be such that the proportion of unsaturated fatty acids is relatively high, that is to say more than 50% of the fat. The unsaturated fatty acids preferably do not have a trans configuration, that is to say the proportion of unsaturated fatty acids having a trans configuration is less than 0.8%, preferably less than 0.5% based on the total amount of fat (weight). In addition, the preparation contains as little linoleic acid as possible.

The proportion of $\Omega$-3 polyunsaturated fatty acids relative to the proportion of $\Omega$-6 polyunsaturated fatty acids must be relatively high. This means that the ratio between $\Omega$-6 fatty acids and $\Omega$-3 fatty acids is preferably less than 3, more preferentially less than 2, for example 1.4.

Cholesterol can be present in the fat composition, for example in an amount of 0.5 to 5% (m/m) of the total amount of fat.

Such a fat composition ensures that the membrane of the cells, in particular nerve cells, has good arrangement and a fluid nature, so that in vivo membrane processes can take place efficiently after activation of the receptor.

The polyunsaturated fatty acids are preferably present in the form of bound fatty acids, for example fatty acids bound to glycerol, such as in the form of triglycerides, but also, and this is preferred, in the form of phospholipids.

Components which have a beneficial effect on total methionine metabolism (TMM) are understood to be the components as described in EP 0 891 719, which is included herein by reference. These components are selected from vitamin B12 and precursors thereof, vitamin B6 and derivatives thereof, folic acid, zinc and magnesium. Preferably these components are selected from vitamin B12 and precursors thereof, vitamin B6 and folic acid. More preferably a combination of folic acid, vitamin B6 and vitamin B12 is used.

Suitable forms of vitamin B12 are cyanocobalamin, hydroxy-, adenosyl- or methyl-cobalamin or mixtures thereof, which may or may not be bound to binding proteins in such a way that these can be completely and easily absorbed in the small intestine. These substances are suitably incorporated in the preparation in an amount such that it contains at least 3 µg, preferably at least 10 µg and in particular 50 to 1000 µg cobalamin per daily dose of the product.

Folic acid must be present in an amount of at least 250 µg, in particular 300 to 1500 µg, per daily dose of the product. Suitable forms are folinic acid, folic acid and methyl derivates thereof, in the non-oxidised or oxidised form.

Pyridoxine or derivatives thereof, such as pyridoxamine or pyridoxal, can be used in the product as suitable sources of vitamin B6. At least 1 mg vitamin B6, preferably 2 to 20 mg vitamin B6, per daily dose is contained in the product.

In addition to $\Omega$-3 polyunsaturated fatty acids and components which have a beneficial effect on methionine metabolism, the preparation according to the invention can also contain phospholipids. These are preferably phosphatidylserine, phosphatidylinositol, phosphatidylcholine and phosphatidylethanolamine. Preferably a mixture of two or more of these phospholipids is used, in particular a mixture that contains at least phosphatidylcholine and phosphatidylserine. The daily dose of phospholipids is preferably at least 0.2 g, more preferentially at least 1 g.

Another characteristic of the phospholipids is the fatty acid group of the phospholipids. These preferably have a composition corresponding to the $\Omega$-3 polyunsaturated fatty acids as described above. This can be achieved by using known interesterification techniques using crude phospholipid mixtures and ingredients rich in the suitable fatty acids as the starting materials.

This can also be achieved by feeding birds with special fats, so that the phospholipid fraction obtained from their eggs has a fatty acid composition that is as similar as possible to the desired composition. Varieties of plants can also be genetically modified so that they contain the active compounds in the correct amounts. An example of this is genetically modified soya where the phospholipid fraction contains additional EPA and/or DHA.

Phospholipids can be obtained from egg yolk or soya and can be isolated using known techniques, for example by acetone extraction and subsequent chromatographic techniques or adsorption methods. If required, synthetic phospholipid fractions can also be used, but this is not preferred.

Other substances which are preferably present in the preparation are components selected from thiamine, pantothenic acid, carnitine, vitamin C, vitamin E, carotenoids, coenzyme Q10 and flavinoids.

Amongst these, carnitine is a preferred compound. This also includes functional equivalents of carnitine, such as salts thereof or alkanoyl- and acyl-carnitines (acetyl-L-carnitine). Carnitine can be incorporated in an amount of 0.1 to 3 g, preferably 0.2 to 1 g per daily dose. Coenzyme Q10 can be incorporated in an amount of 0.8 to 200 mg, preferably 5 to 70 mg per daily dose.

In the preparation of the invention the components are preferably combined with existing agents which increase the amount of neurotransmitter in the synapse. These can be the neurotransmitters themselves, but also derivates thereof, precursors of the neurotransmitters and drugs that are used for this purpose, such as drugs that inhibit the reuptake of the neurotransmitters released in the synapse, such as the so-called serotonin-reuptake inhibitors, or substances that inhibit the metabolic conversion of the neurotransmitters, such as the cholinesterase inhibitors, monoamine oxidase inhibitors and decarboxylation inhibitors. Certain nucleotides or precursors thereof also stimulate the formation of neurotransmitters.

Examples of the neurotransmitters themselves are, for example, dopamine and the known analogues thereof which are already widely used in combating the symptoms of Parkinson's disease. These substances are obtainable in synthetic form. When the preparation of the invention is used, the dosage of these substances can be reduced by as much as 50%.

Known drugs that increase the levels of neurotransmitters, for example serotonin agonists or serotonin reuptake inhibitors, which can be combined with the preparation of the invention are PROZAC™ (fluoxetine), ZOLOFT™ (sertralinc), LUVOX™ (fluvoxamine), REDUX™ (dexfenfluramine), PONDTMIN™ (fenfluramine), MAXALT™ (rizatriptan), IMITREX™ (sumatriptan), ALMOGRAM™ (almotriptan), ZELAPAR™ (selegiline) MIRAPEX™ (pramipexole), PERMAX™ (pergotide), EXELON™ (rivastigmifle), REMILNYL™ (galantamine), ARICEPT™ (donepezil), COGNEX™ (tacrine), Tasaclidine, ERGOSET™ (bromocriptirie) and many other similar drugs. Insulin is also used to stimulate the insulin receptor.

Other examples of neurotransmitters are serotonin, adrenaline, noradrenaline, glutamate, acetylcholine and gamma-aminobutyric acid. These can also be incorporated in the preparation.

Examples of precursors of neurotransmitters are the amino acids L-tryptophan, L-phenylalanine and L-tyrosine. Under certain conditions, serotonin can be formed from L-tryptophan in the body of the animal. Also, for example, dopamine, noradrenaline (norepinephrine) and adrenaline (epinephrine) can be formed under certain conditions from L-phenylalanine and/or L-tyrosine.

Functional equivalents of these amino acids can also be used as precursor for neurotransmitters, such as, for example, N-alkylated forms or esterified forms and salts. An example of a suitable derivative of tryptophan is 5-hydroxytryptophan. However, it is preferable to use proteins or hydrolysed products thereof or peptides. Preferably, the proteins used contain a relatively high concentration of the relevant amino acids. Enriched proteins can also be used, for example obtained by dialysis and membrane filtration techniques. An example of a protein enriched in tryptophan is α-lactalbumin.

The amounts of neurotransmitters or agents which increase the concentration of neuro-transmitters in the synapse are dependent on the nutritional status of the patient and his or her diet. Per daily dose, at least 14 mg/kg body weight phenylalanine+tyrosine, that is to say on average 1 g/day, must be consumed via the complete diet. The product according to the invention preferably contributes at least 50% to this, that is to say at least 0.5 g/day and preferably 0.7-3 g/day. The diet must also provide at least 3.5 mg/kg body weight tryptophan. The product according to the invention preferably contributes at least 50% of this, that is to say at least 130 mg/day. Preferably the preparation contains 200-2200 mg tryptophan per daily dose.

Under certain conditions, acetylcholine can be formed from choline and betaine. Choline can also originate from phosphatidylcholine. It is advantageous that the product contains at least 0.4 g choline equivalents per daily dose, preferably in the form of 0.4 to 2 g betaine or in the form of 3.5 to 18 g phosphatidylcholine, in particular obtained from lecithins with rapeseed, egg or soya as possible source.

Nucleotides play an important role in the formation of acetylcholine. It is preferable to incorporate nucleotides in the preparation, in particular in the form of ribonucleic acids such as, for example, are present in yeast or extracts thereof. Preferably the product contains at least 50 mg nucleobases, including uridine or cytidine, per daily dose. This corresponds to, for example, at least 2.5 g crude brewer's yeast. Instead of the bases it is also possible to use the phosphates thereof, such as the mono-, di- or tri-phosphate (for example uridine monophosphate (UMP)).

A pentose, such as D-ribose, xylitol, L-arabinose or an oligosaccharide or polysaccharide that contains these sugars can also be incorporated in the product instead of or in addition to nucleotides. Oligosaccharides that contain D-ribose and arabans are most preferred. At least 0.5 g of the pentose, preferably 1 to 20 g, is administered per daily dose.

The preparations according to the invention can be used for improving the action of receptors in cells of the central nervous system, in particular for improving the sensitivity of receptors to neurotransmitters. Specific receptors that can be influenced by the preparation of the invention are metabotropic receptors, preferably G protein coupled receptors.

Examples of metabotropic receptors are the seven transmembrane domain receptors which usually function via G proteins, but also single transmembrane domain receptors such as the tyrosine kinase receptor family (growth factors, insulin), the cytokine receptor family (growth hormone, erythropoietin, leptin, prolactin), the serine-threonine kinase receptor family (TGF-beta), the guanylyl cyclase receptor family (atrial natriuretic peptides) and the phosphotyrosine phosphatase family.

Disorders of which the severity can be reduced by increasing the action of the receptor are, in particular, disorders associated with disturbed neurotransmitter functioning. Specific examples of these are Parkinson's disease, Huntington's chorea, epilepsy, schizophrenia, paranoia, depression, sleep disorders, impaired memory function, psychoses, dementia and ADHD and motor disorders such as can arise after, for example, a trauma, stroke and ALS and chronic fatigue syndrome.

In view of the general nature of the improvement in receptor function, in a number of cases it is desirable to add an antagonist. This is, for example, the case when aiming for weight loss. A more rapid effect is obtained if an antagonist for the α-2 receptor is given.

The preparation of the invention can be used both for humans and animals, preferably for humans.

The preparation can be brought into a suitable form and administered either as a pharmaceutical preparation or as a nutritional preparation. Suitable additives and excipients for such preparations are known to those skilled in the art.

EXPERIMENTAL

The chronic dietary intake of essential polyunsaturated fatty acids can modulate learning and memory processes by being incorporated into neuronal and glial plasma membranes. Representatives of the two important polyunsaturated fatty acid families, the n-3 and n-6 types become integrated into membrane phospholipids, where the actual (n-6)/(n-3) ratio can determine membrane fluidity. In the present experiment we studied hippocampal neurotransmitter receptor densities after chronic administration of diets enriched in docosahexaenoic/eicosapentaenoic acid and methionine metabolism stimulating components in a brain hypoperfusion model which mimics decreased cerebral perfusion as it occurs in ageing and dementia.

Sixty 30-day-old Wistar rats were randomly divided into 3 groups of 20. Each group was given a specific diet, the first ordinary chow (placebo), the second group chow of a specific composition S1 and the third group the same feed as Group 2 with additional components (S2); see Table 1. The diets contained identical quantities of proteins, carbohydrates, minerals and energy. At the age of 4 months, two of the four carotid arteries of half of each group of animals were occluded (2VO animals). The other half was subjected to a similar operation without occlusion of the arteries. At the age of 7 months the animals were sacrificed for further investigation. Inter alia, the receptor density in specific parts of the brain was determined with the aid of labelling using a radioactive marker substance.

Three receptor types, the muscarinic 1, serotonergic 1A and the glutaminergic NMDA receptors were labelled in hippocampal slices by autoradiographic methods. The increased ratio of n-3 fatty acids in combination with additional dietary supplements (table 1) enhanced the density of the serotonergic 1A and muscarinic 1 receptors (Table 2), but no major effects were found on the NMDA receptors. Since the examined receptor types reacted differently to the dietary supplementation, it can be concluded that besides changes in membrane fluidity, the biochemical regulation of receptor sensitivity may also play a role in increasing hippocampal receptor density. The NMDA receptor differs from the here investigated $M_1$ and 5-HT1 A receptors in that the NMDA receptor is an ion channel receptor versus the other two G protein-coupled, metabotropic receptors. NMDA receptors are ionotropic receptors which need no major conformational changes like the metabotropic receptors during binding. Metabotropic receptors like the muscarinic1 acetylcholine receptor and the serotonergic 5-HT1 receptor bind transmitter and through a series of conformational changes bind to G proteins and activate them. These conformations are facilitated when membranes are fluid.

TABLE 1

| Component | Placebo g/100 g | S1 g/110 g | S2 g/110 g |
| --- | --- | --- | --- |
| EPA | — | 0.5 | 0.5 |
| DHA | — | 0.37 | 0.37 |
| ALA | 0.155 | 0.137 | 0.184 |
| LA | 0.640 | 1.321 | 1.661 |
| AA | — | 0.2 | 0.2 |
| β-carotene | — | 0.02 | 0.02 |
| Flavonoids | — | 0.2 | 0.2 |
| Folate | 0.000784 | 0.001 | 0.001 |

TABLE 1-continued

| Component | Placebo g/100 g | S1 g/110 g | S2 g/110 g |
| --- | --- | --- | --- |
| Selenium | 0.000019 | 0.00004 | 0.00004 |
| Vitamin B6 | 0.00153 | 0.00172 | 0.00172 |
| Vitamin B12 | 0.00005 | 0.00012 | 0.00012 |
| Vitamin C | — | 0.2 | 0.2 |
| Vitamin E | 0.0063 | 0.3 | 0.3 |
| Acetylcarnitine | | | 0.6 |
| Choline | | | 0.4 |
| Phosphatidylcholine | | | 0.2 |
| Phosphatidylserine | | | 0.2 |
| Q10 | | | 0.03 |
| Thiamine | 0.002 | | 0.2 |
| Tyrosine | 0.944 | | 1 |
| Tryptophan | 0.232 | | 1 |

TABLE 2

(nCi/mg tissue)

| | Acetylcholine receptor | | Serotonin receptor | |
| --- | --- | --- | --- | --- |
| | stratum oriens | Stratum radiatum | Stratum oriens | stratum radiatum |
| Placebo | 2.8 | 3.1 | 7.3 | 9.6 |
| S1 | 3.2 | 3.6 | 7.8 | 10.8 |
| S2 | 3.3 | 3.7 | 8.5 | 11.6 |

The invention claimed is:

1. A composition comprising:
   ω-3 polyunsaturated fatty acids comprising docosahexaenoic acid and eicosapentaenoic acid;
   at least one of (i) vitamin B12 and (ii) one or more of vitamin B6, pyridoxine, pyridoxamine and pyridoxal;
   folic acid in a daily dose amount of at least 250 μg;
   uridine and/or one or more of its phosphates.

2. The composition according to claim 1, wherein said ω-3 polyunsaturated fatty acids are in a daily dose amount of at least 120 mg.

3. The composition according to claim 2, wherein said ω-3 polyunsaturated fatty acids in a daily dose amount of at least 350 mg.

4. The composition according to claim 1, wherein said preparation comprises said vitamin B12 in a daily dose amount of at least 3 μg cobalamin equivalents.

5. The composition according to claim 1, wherein said preparation comprises said one or more of vitamin B6, pyridoxine, pyridoxamine and pyridoxal in a daily dose amount of at least 1 mg.

6. The composition according to claim 1, further comprising phospholipids in a daily dose amount of at least 0.2 g.

7. The composition according to claim 1, further comprising carnitine in a daily dose amount of 0.1-3 g.

8. The composition according to claim 1, further comprising a daily dose amount of at least 0.5 g of the sum of tyrosine and phenylalanine.

9. The composition according to claim 1, further comprising said tryptophan in a daily dose amount of at least 130 mg.

10. The composition according to claim 1, further comprising a daily dose amount of 0.4-2 g of betaine or 3.5 to 18 g of phosphatidyicholine.composition

* * * * *